(12) United States Patent
Hibbs

(10) Patent No.: US 6,759,563 B1
(45) Date of Patent: Jul. 6, 2004

(54) LIQUID PHASE ADSORPTIVE SEPARATION WITH HEXANE DESORBENT AND PARAFFIN ISOMERIZATION

(75) Inventor: Frederick M. Hibbs, Shalford (GB)

(73) Assignee: UOP LLC, Des Plaines, IL (US)

( * ) Notice: Subject to any disclaimer, the term of this patent is extended or adjusted under 35 U.S.C. 154(b) by 419 days.

(21) Appl. No.: 09/973,334

(22) Filed: Oct. 9, 2001

(51) Int. Cl.[7] ................................................. C07C 5/22
(52) U.S. Cl. ........................ 585/737; 585/734; 585/738; 585/826
(58) Field of Search ................................ 585/734, 737, 585/738, 826

(56) References Cited

U.S. PATENT DOCUMENTS

| | | | |
|---|---|---|---|
| 2,859,173 A | * | 11/1958 | Hess et al. ............. 208/92 |
| 2,966,528 A | | 12/1960 | Haensel ............. 260/666 |
| 3,227,647 A | * | 1/1966 | Krane ............. 208/310 R |
| 3,755,144 A | | 8/1973 | Asselin ............. 208/95 |
| 4,210,771 A | | 7/1980 | Holcombe ............. 585/701 |
| 4,717,784 A | | 1/1988 | Stem et al. ............. 585/738 |
| 4,804,802 A | | 2/1989 | Evans et al. ............. 585/734 |
| 4,956,521 A | | 9/1990 | Volles ............. 585/826 |
| 4,982,048 A | * | 1/1991 | Stem et al. ............. 585/751 |
| 5,043,525 A | | 8/1991 | Haizmann et al. ............. 585/737 |
| 5,059,741 A | * | 10/1991 | Foley ............. 585/734 |
| 5,326,925 A | | 7/1994 | Sachtler ............. 585/736 |
| 5,530,173 A | * | 6/1996 | Funk et al. ............. 585/737 |
| 5,602,291 A | * | 2/1997 | Minkkinen et al. ............. 585/738 |
| 5,744,684 A | * | 4/1998 | Zinnen et al. ............. 585/737 |
| 6,069,289 A | * | 5/2000 | Dandekar et al. ............. 585/820 |
| 6,395,950 B1 | * | 5/2002 | Rice ............. 585/738 |

* cited by examiner

Primary Examiner—Walter D. Griffin
(74) Attorney, Agent, or Firm—John G. Tolomei; Frank S. Molinaro; Maryann Maas

(57) ABSTRACT

A combination isomerization and liquid phase adsorptive separation process has been developed. In this arrangement, a $C_5+$ naphtha stream is split into a heavy hydrocarbon stream comprising normal heptane and higher boiling hydrocarbons, an isomerization and adsorption zone feed stream comprising pentanes and lower boiling hydrocarbons, and a desorbent stream containing hexanes. The isomerization and adsorption zone feed stream is combined with an isomerization section effluent to form a combined feed to an adsorptive separation section. In the adsorption separation section, normal pentanes are selectively adsorbed on an adsorbent material, and a raffinate stream comprising hexanes and isoparaffins is recovered and passed to a deisohexanizer column. A desorbent stream containing normal hexane is recovered as a sidecut from the deisohexanizer column and is combined with the desorbent stream containing the hexanes from the naphtha splitter to supply the desorbent for the adsorptive separation section. The extract stream that is recovered from the adsorptive separation section is passed to the isomerization section. A bottoms stream comprising $C_7$ and higher boiling hydrocarbons is withdrawn from the bottom of the deisohexanizer column. A high-octane isomerate is taken overhead from the deisohexanizer column as a product stream.

34 Claims, 2 Drawing Sheets

LIQUID PHASE ADSORPTIVE SEPARATION WITH HEXANE DESORBENT AND PARAFFIN ISOMERIZATION

BACKGROUND OF THE INVENTION

This invention relates generally to the isomerization of hydrocarbons. This invention relates more specifically to the isomerization of light paraffins using a solid catalyst and the separation of more highly branched paraffins from less highly branched and non-branched paraffins by liquid phase adsorptive separation and distillation.

BACKGROUND OF THE INVENTION

High-octane gasoline is required for modern gasoline engines. Formerly it was common to accomplish octane number improvement by the use of various lead-containing additives. As lead is phased out of gasoline for environmental reasons, it has become increasingly necessary to rearrange the structure of the hydrocarbons used in gasoline blending in order to obtain high-octane levels. Catalytic reforming and catalytic isomerization are two widely used processes for this upgrading.

A gasoline blending pool normally includes $C_4$ and heavier hydrocarbons having boiling points of less than 215° C. (419° F.) at atmospheric pressure. This range of hydrocarbons includes $C_4$–$C_6$ paraffins and especially the $C_5$ and $C_6$ normal paraffins that have relatively low octane numbers. The $C_4$–$C_6$ hydrocarbons have the greatest susceptibility to octane improvement by lead addition and were formerly upgraded in this manner. Octane improvement can also be obtained by using isomerization to rearrange the structure of the paraffinic hydrocarbons into branched-chain paraffins or reforming to convert the $C_6$ and heavier hydrocarbons to aromatic compounds. Normal $C_5$ hydrocarbons are not readily converted into aromatics, therefore, the common practice has been to isomerize these lighter hydrocarbons into corresponding branched-chain isoparaffins. Although the $C_6$ and heavier hydrocarbons can be upgraded into aromatics through hydrocyclization, the conversion of $C_6$'s to aromatics creates higher density species and increases gas yields with both effects leading to a reduction in liquid volume yields. Therefore, it is common practice to charge the $C_6$ paraffins to an isomerization unit to obtain $C_6$ isoparaffin hydrocarbons. Consequently, octane upgrading commonly uses isomerization to convert $C_6$ and lighter boiling hydrocarbons to higher octane $C_6$ isoparaffin hydrocarbons and reforming to convert $C_7$ and higher boiling hydrocarbons to higher octane aromatic and isoparaffin hydrocarbons.

The effluent from an isomerization reaction zone will contain a mixture of more highly branched and less highly branched paraffins. In order to further increase the octane of the products from the isomerization zone, normal paraffins, and sometimes less highly branched isoparaffins, are typically recycled to the isomerization zone along with the feed stream in order to increase the ratio of less highly branched paraffins to more highly branched paraffins entering the isomerization zone. A variety of methods are known to treat the effluent from the isomerization zone for the recovery of normal paraffins and monomethyl branched isoparaffins for recycling these less highly branched paraffins to the isomerization zone.

U.S. Pat. No. 2,966,528 B1 issued to Haensel discloses a process for the isomerization of $C_6$ hydrocarbons and the adsorptive separation of normal hydrocarbons from branched chain hydrocarbons. The process adsorbs normal hydrocarbons from the effluent of the isomerization zone and recovers the unadsorbed hydrocarbons as product, desorbs straight chain hydrocarbons using a normal paraffin desorbent, and returns the desorbent and adsorbed straight chain hydrocarbons to the isomerization zone.

U.S. Pat. No. 3,755,144 B1 shows a process for the isomerization of a pentane/hexane feed and the separation of normal paraffins from the isomerization zone effluent. The isomerization zone effluent is separated by an adsorbent separation zone that includes facilities for the recovery of desorbent from the normal paraffin containing stream that is recycled to the isomerization zone. An extract stream that contains isoparaffins is sent to a deisohexanizer column that separates isopentane and dimethyl butane as a product stream and provides a recycle stream of less branched isohexane that is returned to the isomerization zone.

U.S. Pat. Nos. 4,717,784 B1 and 4,804,802 B1 disclose processes for the isomerization of a hydrocarbon feed and the use of adsorptive separation to generate normal paraffin and monomethyl-branched paraffin recycle streams. The effluent from the isomerization zone enters an adsorbent separation zone that contains a 5A-type sieve and a ferrierite-type sieve that adsorb normal paraffins and monomethyl-branched paraffins, respectively.

U.S. Pat. No. 4,804,802 B1 discloses steam or hydrogen as the desorbent for desorbing the normal paraffins and monomethyl-branched paraffins from the adsorption section and teaches that steam or hydrogen may be recycled with the normal paraffins or monomethyl-branched paraffins to the isomerization zone.

One method of separating normal paraffins from isoparaffins uses adsorptive separation under liquid phase conditions. In such methods, the isomerization effluent contacts a solid adsorbent having a selectivity for normal paraffins to effect the selective adsorption of normal paraffins and allow recovery of the isoparaffins as a high-octane product. Contacting the normal paraffin-containing adsorbent with the desorbent material in a desorption step removes normal paraffins from the adsorbent for recycle to the isomerization zone. Both the isoparaffin and normal paraffin-containing streams undergo a separation for the recovery of desorbent before the isoparaffins are recovered as a product and the normal paraffins recycled to the isomerization zone. Liquid phase adsorption has been carried out in conventional swing bed systems as shown in U.S. Pat. No. 2,966,528 B1. The use of simulated moving bed systems for the selective adsorption of normal paraffins is also known and disclosed in U.S. Pat. No. 3,755,144 B1. Simulated moving bed systems have the advantage of increasing recovery and purity of the adsorbed and non-adsorbed components in the isomerization zone effluent for a given unit of adsorbent material.

In liquid phase adsorption systems, the adsorbent contains selective pores that will selectively adsorb at least one component in the feed mixture. The selective pore volume is limited and the quantity of such pores must accommodate the desired volume of components to be adsorbed from the feed mixture. The desorbent material is also a selectively adsorbed component. Therefore, an extract column is typically used to recover desorbent, otherwise any desorbent that passes through the reactors of the isomerization zone and enters the adsorption section increases the amount of adsorbed component in the feed mixture and requires additional adsorbent. If the quantity of selectively adsorbed components is increased without increasing the available selective pore volume for a given unit of feed, it was is believed that the purity of the extract and raffinate streams from the adsorption section decreased. Therefore, the extract column has been viewed as necessary for the desorption stage of the adsorption section since the loaded adsorbent contains normal paraffins and desorbent material as adsorbed components and all of these adsorbed components must be displaced by the desorbent. Without the extract column, desorbent flow during the desorption step would increase if traditional desorbent to pore volume ratios are maintained thereby placing a greater quantity of desorbent in circulation and increasing the amount of selective pore volume needed during the feed step of the adsorption process. Under the conventional system, without some method of rejecting desorbent material from the recycled extract stream, the selective pore volume and desorbent requirements would continue to progressively increase.

Most moving bed adsorption processes also use a desorbent material that has a different composition than the primary components in the feed stream to the adsorption section. As a result, the desorbent material is typically recovered from the raffinate material that it has desorbed for reuse in the adsorption section. It has been the usual practice to use a raffinate column to separate the desorbent material from the raffinate stream. U.S. Pat. No. 5,043,525 B1 teaches that the combination of an isomerization zone for the isomerization of $C_5$–$C_6$ paraffins and an adsorptive separation section for the recycle of low octane paraffins to the isomerization section can be operated with a single fractionation column for the separation of raffinate, extract, product, desorbent and heavier hydrocarbon components.

SUMMARY OF THE INVENTION

In broad terms, the invention is an arrangement for a combination of an isomerization section for the isomerization of $C_5$ and $C_6$ paraffins and an adsorptive separation section for the separation of the isomerization zone effluent. This arrangement is structured such that an overall feed stream is separated in a first fractionation zone, preferably a naphtha splitter column, to provide feed and desorbent to an adsorption section. Effluent from an isomerization zone along with the feed generated in the first fractionation zone enter an adsorption section that is used to separate the adsorption section feed and effluent into a raffinate stream and an extract stream. The separation is conducted by contacting the adsorption section feed and effluent with an adsorbent and desorbing the adsorbed components from the adsorbent using the desorbent from the first fractionation zone and desorbent from a second fractionation zone. The raffinate from the adsorption section enters a second fractionation zone, preferably a deisohexanizer, that supplies an overhead isomerate product stream, a bottoms stream of heavy hydrocarbons and a sidecut stream of desorbent material comprising at least normal hexane. This arrangement also increases the octane of the isomerate product recovered overhead from the deisohexanizer through the recovery of monomethylpentanes with the desorbent material as it is removed from the deisohexanizer column. The monomethylpentanes are ultimately recycled through the isomerization zone and converted to higher-octane isomers. The extract stream is passed to the isomerization zone for the generation of isomerized products. The isomerization zone effluent is recycled to the adsorption section. In a specific embodiment of the invention, the naphtha splitter column and/or the deisohexanizer may be divided wall columns. In another specific embodiment of the invention, the overhead stream from the first fractionation zone may be routed past the adsorption zone and be combined with the extract and introduced directly to the isomerization zone. Other objects, embodiments, and aspects of this invention are described in the following detailed description of the invention.

DETAILED DESCRIPTION OF THE INVENTION

This invention uses the combination of an isomerization zone and an adsorptive separation section for the isomerization of $C_5$ and $C_6$ paraffins and the separation of the isomerization zone effluent. The invention is not restricted to any particular type of isomerization zone or adsorptive separation section. The isomerization zone can consist of any type of isomerization zone that takes a stream of $C_5$–$C_6$ straight chain hydrocarbons or a mixture of straight chain and branched chain hydrocarbons and converts straight chain hydrocarbons in the feed mixture to branched chain hydrocarbons and branched hydrocarbons to more highly branched hydrocarbons thereby producing an isomerization effluent having branched chain and straight chain hydrocarbons. The adsorption section is preferably liquid phase and can utilize any type of well-known adsorption process such as a swing bed, simulated moving bed, or other schemes for contacting the adsorbent with the feed mixture and desorbing the feed mixture from the adsorbent with the desorbent material.

Suitable feedstocks for this process will include $C_5$ and $C_6$ hydrocarbons. At minimum, the feed will include normal hexane and normal pentane. The typical feed for this process will be a naphtha feed with an initial boiling point in the range of normal butane. The feedstocks that can be used in this invention include hydrocarbon fractions rich in $C_4$–$C_6$ normal paraffins. The term "rich" is defined as a stream having more than 40% of the mentioned component. It is preferred that the feed contains at least 10% and preferably at least 20% normal pentanes. Another requirement of the feed is that it contains enough normal hexane to supply the desorbent requirements of this invention. Useful feedstocks include light natural gasoline, light straight-run naphtha, gas oil condensates, light raffinates, light reformate, light hydrocarbons, and straight-run distillates having distillation end points of about 80° C. (176° F.) and containing substantial quantities of $C_4$–$C_6$ paraffins. The feed may also contain low concentrations of unsaturated hydrocarbons and hydrocarbons having more than 6 carbon atoms. The concentration of these materials should be limited to 10 wt. % for unsaturated compounds and 20 wt. % for heavier hydrocarbons in order to restrict hydrogen consumption in cracking reactions.

Figure 1:
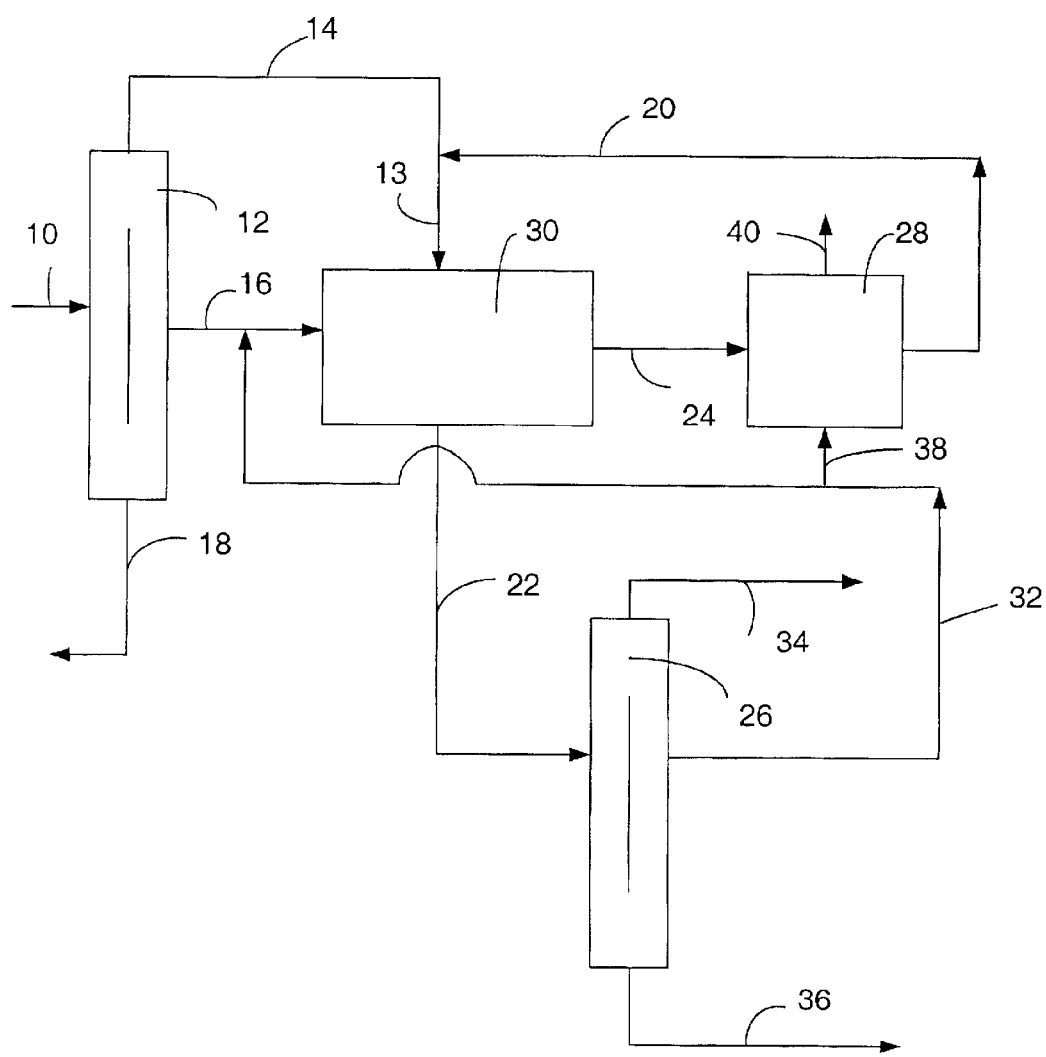
FIG. 1 is a schematic diagram of a flow arrangement for a combination isomerization and adsorption process arranged in accordance with this invention.
Figure 2:
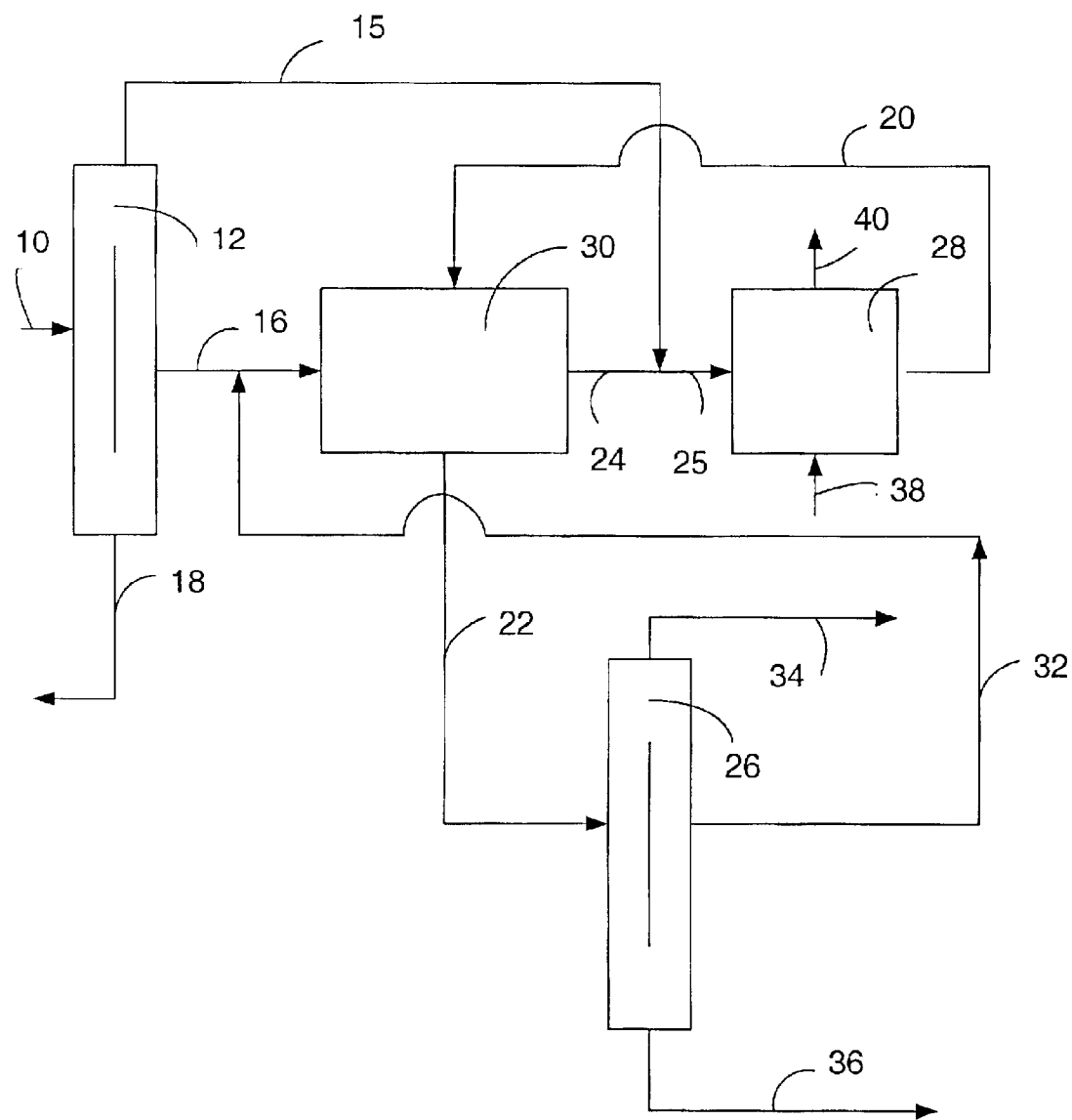
FIG. 2 is a schematic diagram of an alternative flow arrangement for a combination isomerization and adsorption process arranged in accordance with this invention.

This application is described primarily with reference to the embodiment shown in FIG. 1. Reference to the specific arrangement for this invention is not meant to limit it to the details disclosed therein. FIG. 2 depicts an alternative embodiment of the invention and is discussed in greater detail in the Example. FIGS. 1 and 2 are schematic illustrations and do not show a number of details for the process arrangements such as pumps, compressors, valves, stabilizers and recycle lines which are well known to those skilled in the art.

The overall process of the invention begins by separating heptane and higher boiling hydrocarbons in the feed (if present) from hexanes and separating pentanes and hydrocarbons boiling below the pentanes from the hexanes. FIG. 1 shows an arrangement wherein a $C_5+$ naphtha is charged by line 10 to a naphtha splitter column 12. Naphtha splitter column 12 separates the heptanes and any higher boiling hydrocarbons from the hexanes and pentanes plus lower boiling hydrocarbons. A line 14 carries the pentanes and lower boiling hydrocarbons overhead from naphtha splitter column 12 and line 16 carries hexanes from a side cut from naphtha splitter column 12. Naphtha splitter column 12 is not an essential part of this invention but will be used in most arrangements when processing a combined normal pentane and normal hexane-rich feed. The side cut from naphtha splitter column 12 containing a substantial quantity of the normal hexane that is charged to the process then becomes available for use as desorbent in the separation zone is discussed below. An advantage of the present invention is the production of an internal desorbent for use in the adsorption section; no external desorbent is required. In one embodiment, the overhead 14 from naphtha splitter column 12 containing a substantial quantity of the pentanes that are charged to the process become the feed to the separation zone. Of course, in certain situations where a separate normal hexane-rich stream is available, the process may be operated without a splitter.

The naphtha splitter column 12 overhead in line 14 is preferably mixed with effluent from the isomerization zone in line 20 and enters the adsorption section 30 where it is contacted with an adsorbent in an adsorption zone. The combined streams of 14 and 20 will be referred to generally as the adsorption zone feed stream, line 13. In another embodiment, however, the overhead stream from naphtha splitter column 12 may bypass the adsorption zone and be combined with the extract stream from the adsorption zone. Specifically, FIG. 2 shows the overhead stream from naphtha splitter column 12 as line 15 which is combined with the extract stream from the adsorption zone in line 24. The combined stream 25, is introduced into isomerization zone 28. The effluent of isomerization zone 28 is conducted in line 20 as the feed to the adsorption zone 30. In the embodiment shown in FIG. 2 any isopentane present in line 15 is passed to isomerization zone 28 and may increase the volume of material passed through isomerization zone 28. In the embodiment of FIG. 1, any isopentane present in line 14 is removed prior to the isomerization zone and thus may decrease the volume of material passed through isomerization zone 28. The description below will refer to the embodiment of FIG. 1 with the understanding that the overhead stream from naphtha splitter column 12 may be routed around the adsorption zone and combined with the stream entering isomerization zone 28 as shown in FIG. 2 (discussed in detail in the Example).

One purpose of the adsorption section of this invention is to remove the normal pentane fraction from the effluent of the isomerization zone for recycle to the isomerization zone. In one embodiment of the invention, another purpose of the adsorption section is to separate the normal pentane fraction from the splitter column from any isopentane that may be present in the splitter column overhead. These purposes are successfully met as demonstrated, for example, in FIG. 1, where a normal pentane containing stream 14 from naphtha splitter column 12 is combined with the normal pentane containing stream 20 from the isomerization zone effluent and the combination 13 is introduced to the adsorption zone 30. Isopentane that was present in the splitter column overhead is separated in adsorption zone 30 and is not passed to the isomerization zone 28 thereby reducing the volume of the stream sent to the isomerization zone, and reducing the size of the isomerization zone. At the same time, normal pentane from the isomerization zone effluent is separated and recycled to isomerization zone 28.

This process is especially suited for adsorption systems that use multiple ports for supplying the process streams to the adsorbent and divide the adsorbent into a plurality of zones for adsorbing normal paraffins, recovering isoparaffins, purifying the adsorbent, and desorbing the normal paraffins. Well-known processes of this type are the simulated countercurrent moving bed system and the moving bed countercurrent flow systems. Such systems have significantly greater separation efficiency than fixed molecular sieve bed systems. In either the moving bed or simulated moving bed processes, the retention and displacement operations are continuously taking place, which allows both continuous production of an extract and a raffinate stream and the continual use of feed and desorbent streams. One preferred embodiment of this process utilizes what is known in the art as the "simulated moving bed countercurrent flow system". The operating principles and sequence of such flow system are described in U.S. Pat. No. 2,985,589 B1 incorporated herein by reference. In such a system it is the progressive movement of multiple liquid access points down an adsorbent chamber that simulates the upward movement of adsorbent contained in the chamber.

A number of specially defined terms are used in describing the simulated moving bed processes. The term "adsorption zone feed stream" indicates a-stream in the process through which adsorption zone feed material passes to the adsorbent. Adsorption zone feed material comprises one or more extract components and one or more raffinate components. An "extract component" is a compound or type of compound that is more selectively retained by the adsorbent while a "raffinate component" is a compound or type of compound that is less selectively retained. In this process normal hydrocarbons from the feed stream and the isomerization zone effluent are extract components while isomerized products, branched chain hydrocarbons and cyclic hydrocarbons are raffinate components. The term "extract component" as used herein refers to a more selectively retained compound such as normal hydrocarbons in this process. The term "displacement fluid" or "desorbent" shall mean generally a material capable of displacing an extract component. The term "desorbent stream" or "desorbent input stream" indicates the stream through which desorbent passes to contact the adsorbent. The term "raffinate output stream" means a stream through which most of the raffinate components are removed from the adsorbent. The composition of the raffinate stream can vary from about 100% desorbent to essentially 100% raffinate components. The term "extract stream" or "extract output stream" means a stream through which an extract material that has been displaced by a desorbent is removed from the adsorbent. The composition of the extract stream can also vary from about 100% desorbent to essentially 100% extract components.

The term "selective pore volume" of the adsorbent is defined as the volume of the adsorbent that selectively retains extract components from the feedstock. The term "non-selective void volume" of the adsorbent is the volume of the adsorbent that does not selectively retain extract components from the feedstock. This non-selective void volume includes the cavities of the adsorbent which are not capable of selectively retaining extract components and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent.

When adsorbent "passes" into an operational zone (hereinafter defined and described) its non-selective void volume together with its selective pore volume carries fluid into that zone. The non-selective void volume is utilized in determining the amount of fluid that should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in the non-selective void volume of the adsorbent, it, in most instances, comprises less selectively retained feed components.

In the preferred simulated moving bed process only four of the access lines are active at any one time: the feed input stream, displacement or desorbent fluid inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a pump may provide a liquid flow-down the adsorbent chamber. As an active liquid access point moves through a cycle, that is, from the top of the chamber to the bottom, the chamber circulation pump moves liquid through different zones which require different flow rates. A programmed flow controller may be provided to set and regulate these flow rates.

The active liquid access points effectively divide the adsorbent chamber into separate zones, each of which has a different function. In this embodiment of the process, it is generally necessary that three separate operational zones are present in order for the process to take place, although in some instances an optional fourth zone may be used.

The retention or extract zone, zone 1, is defined as the adsorbent located between the feed inlet stream and the raffinate outlet stream. In this zone, the adsorption zone feed contacts the adsorbent, an extract component is retained, and a raffinate stream is withdrawn. Since the general flow through zone 1 is from the adsorption zone feed stream, which passes into the zone, to the raffinate stream, which passes out of the zone, the flow in this zone is considered to be in a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the displacement of any raffinate material retained within the selective pore volume of the adsorbent. Purification is achieved by passing a portion of extract stream material leaving zone 3 into zone 2 at zone 2's upstream boundary to effect the displacement of raffinate material. The flow of material in zone 2 is in a downstream direction from the extract outlet stream to the feed inlet stream.

Immediately upstream of zone 2 with respect to the fluid flowing in zone 2 is the displacement or desorption zone, zone 3. The desorption zone is defined as the adsorbent between the desorption inlet and the extract outlet stream. The function of the desorption zone is to allow a desorbent which passes into this zone to displace the extract component that was retained in the adsorbent during a previous contact with feed in zone 1 in a prior cycle of operation. The flow of fluid in zone 3 is essentially in the same direction as that of zones 1 and 2.

In some instances, an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream removed from zone 1 can be passed into zone 4 to displace desorbent present in that zone out of the zone into the desorption zone. Zone 4 will contain enough desorbent so that raffinate material present in the raffinate stream passing out of zone 1 and into zone 4 can be prevented from passing into zone 3 and contaminating the extract stream removed from zone 3. In the instances in which the fourth operational zone is not utilized, the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, displacement fluid input and raffinate output streams pass are advanced in the same direction through the adsorbent bed. Both the manifold arrangement and disc valve are known in the art. Specifically rotary disc valves that can be utilized in this operation can be found in U.S. Pat. Nos. 3,040,777 B1 and 3,422,848 B1, incorporated herein by reference. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For example, in some operations the buffer zone can contain a minor amount of adsorbent as compared to the adsorbent required for the retention and purification zones. In instances where desorbent can easily displace extract material from the adsorbent, a relatively small amount of adsorbent will be needed in a desorption zone as compared to the adsorbent needed in the retention zone or purification zone. Since it is not required that the adsorbent is located in a single column, the use of multiple chambers or a series of columns is within the scope of the invention.

It is not necessary for all of the input or output streams to be used simultaneously, and, in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps, which during the normal operations do not function as a conduit through which material passes into or out of the process.

Reference can be made to D. B. Broughton U.S. Pat. No. 2,985,589 B1, and to a paper entitled "Continuous Adsorptive Processing—A New Separation Technique" by D. B. Broughton presented at the 34th Annual Meeting of the Society of Chemical Engineers at Tokyo, Japan on Apr. 2, 1969, the patent incorporated herein by reference, for further explanation of the simulated moving bed countercurrent process flow scheme.

Although both liquid and vapor phase operations can be used in many adsorptive type separation processes, liquid-phase operation is preferred for this process because of the lower temperature requirements and because of the higher yields of extract product that can be obtained with liquid-phase operation over those obtained with vapor-phase operation. Extract conditions will, therefore, include a pressure sufficient to maintain liquid phase. Desorption conditions will include the same range of temperatures and pressures as used for extract conditions.

In the operation of this process, at least a portion of the raffinate output stream will be passed directly to a fractionation zone. The fractionation zone will typically be a single fractionation column, the general design and operation of which is well known to the separation art. In FIG. 1, line 22 passes the raffinate directly to deisohexanizer 26, which will be discussed in detail below.

The extract stream from the adsorption zone carried by line 24 will contain primarily normal hexane and normal pentane and may contain some monomethylpentanes. Therefore, the hydrocarbon components in the extract stream are susceptible to octane improvement by further processing through the isomerization zone. Hydrogen may be admixed with the extract stream from the adsorption zone in an amount that will provide a hydrogen to hydrocarbon molar ratio of from 0.01 to 10 in the effluent from the isomerization zone. Preferably, the hydrogen to hydrocarbon molar ratio is in the range of 0.05 to 5. Alternatively, hydrogen may be introduced directly to the isomerization zone, line 38. The hydrogen may be recycled to the isomerization zone or removed, line 40. Although no net hydrogen is consumed in the isomerization reaction, the isomerization zone will have a net consumption of hydrogen often referred to as the stoichiometric hydrogen requirement that is associated with a number of side reactions that occur. These side reactions include saturation of olefins and aromatics, cracking and disproportionation. For extract streams having a high level of unsaturates, satisfying the stoichiometric hydrogen will require a higher hydrogen to hydrocarbon molar ratio for the feed at the inlet of the isomerization zone. Hydrogen in excess of the stoichiometric amounts for the side reactions is often maintained in the reaction zone to provide stability and conversion by compensating for variation in feed stream compositions that alter the stoichiometric hydrogen requirements. Higher hydrogen to hydrocarbon molar ratios are often used to prolong catalyst life by suppressing side reactions such as cracking and disproportionation. When such side reactions occur, they can reduce conversion and lead to formation of carbonaceous compounds, usually referred to as coke, that foul the catalyst.

The hydrogen to hydrocarbon molar ratio in isomerization zones that use a chlorided platinum alumina catalyst can be reduced significantly. In such cases, it is desirable to reduce the amount of hydrocarbon that enters the isomerization zone such that the hydrogen to hydrocarbon molar ratio of the effluent from the isomerization zone is less than 0.05. Reduced hydrogen to hydrocarbon molar ratios have been used based on the finding that the amount of hydrogen required for suppressing coke formation need not exceed dissolved hydrogen levels. The amount of hydrogen in solution at the normal conditions of the isomerization zone effluent is preferably in a ratio of from 0.02 to 0.01. The amount of excess hydrogen over the stoichiometric requirement that is required for good stability and conversion is in a ratio of from 0.01 to less than 0.05.

When the hydrogen to hydrocarbon molar ratio exceeds 0.05, it is not economically desirable to operate the isomerization zone without the recycle of hydrogen to the isomerization zone. Therefore, in such cases, recovery facilities for hydrogen from the effluent will be provided as hereinafter described. Hydrogen may be added to the feed mixture in any manner that provides the necessary control for the addition of the hydrogen.

The effluent or extract from the adsorption section is contacted in the isomerization zone with an isomerization catalyst. The catalyst composites that can be used in the isomerization zone include traditional isomerization catalysts. Such catalysts include high chloride catalyst on an alumina base containing platinum, and crystalline aluminosilicates or crystalline zeolites. Suitable catalyst compositions of this type will exhibit selective and substantial isomerization activity under the operating conditions of the process.

The preferred isomerization catalyst for this invention is a chlorided platinum alumina catalyst. The aluminum is preferably an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt. % of the platinum. Other platinum group metals may be present in a concentration of from 0.1 to 0.25 wt. %. The platinum component may exist within the final catalytic composite as an oxide or halide or as an elemental metal. The presence of the platinum component in its reduced state has been found most suitable for this process. The chloride component termed in the art as "a combined chloride" is present in an amount from about 2 to about 10 wt. % based upon the dry support material. The use of chloride in amounts greater than 5 wt. % have been found to be the most beneficial for this process. The inorganic oxide preferably comprises alumina and more preferably gamma-alumina, eta-alumina, and mixtures thereof.

There are a variety of ways for preparing the catalytic composite and incorporating the platinum metal and the chloride therein. The method that has shown the best results in this invention prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of halogen must be incorporated into the catalyst by the addition or formation of aluminum chloride to or on the platinum-aluminum catalyst base. An alternate method of increasing the halogen concentration in the final catalyst composite is to use an aluminum hydrosol to form the aluminum carrier material such that the carrier material also contains at least a portion of the chloride. Halogen may also be added to the carrier material by contacting the calcined carrier material with an aqueous solution of the halogen acid such as hydrogen chloride.

It is generally known that high chlorided platinum-alumina catalysts of this type are highly sensitive to sulfur and oxygen-containing compounds. Therefore, the use of such catalysts requires that the streams fed to the isomerization zone should be relatively free of such compounds. A sulfur concentration no greater than 0.5 ppm is generally required. The presence of sulfur in the stream serves to temporarily deactivate the catalyst by platinum poisoning. Activity of the catalyst may be restored by hot hydrogen stripping of sulfur from the catalyst composite or by lowering the sulfur concentration in the incoming stream to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$–$C_5$ oxygenates, that can decompose to form water, can only be tolerated in very low concentrations. In general, this requires a limitation of oxygenates in the feed to about 0.1 ppm or less. The extract from the adsorption zone, or the feed stream to the splitter column may be treated by any method that will remove water and sulfur compounds. Sulfur may be removed from the feed stream by hydrotreating. A variety of commercial dryers are available to remove water from the feed components. Adsorption processes for the removal of sulfur and water from hydrocarbon streams are also well known to those skilled in the art.

As a class, the crystalline aluminosilicate or crystalline zeolite catalysts comprise crystalline zeolitic molecular sieves having an apparent pore diameter large enough to adsorb neopentane. A silica alumina molar ratio $SiO_2$:$Al_2O_3$ of greater than 3; less than 60 and preferably between 15 and 30 is desirable. In preferred form, the zeolite will contain an equivalent percentage of alkali metal cations and will have those $AlO_4$-tetrahedra not associated with alkali metal cations, either not associated with any metal cations or associated with divalent or other polyvalent metal cations. Usually the molecular sieve is a mordenite molecular sieve, which is essentially in the acid form or is converted to the acid form. Particularly preferred catalysts of this type for isomerization are disclosed in detail in U.S. Pat. Nos. 3,442,794 B1 and 3,836,597 B1.

A preferred composition of zeolitic catalyst for use in the present invention comprises a Group VIII noble metal, a hydrogen form crystalline aluminosilicate, and a refractory inorganic oxide with the catalyst composition having a surface area of at least 580 $m^2/g$. Significant improvements in isomerization performance are realized when the surface area of the catalytic composite is at or above 580 $m^2/g$. A Group VIII metal is incorporated into the catalytic composite to supply a hydrogenation/dehydrogenation function and the preferred Group VIII noble metal is platinum. The Group VIII noble metal is present in an amount from about 0.01 to 5% by weight of the composite and preferably in an amount of at least 0.15% by weight but not over 0.35% by weight.

The zeolitic catalytic composite may also contain a catalytically effective amount of a promoter metal such as tin, lead, germanium, cobalt, nickel, iron, tungsten, chromium, molybdenum, bismuth, indium, gallium, cadmium, zinc, uranium, copper, silver, gold, tantalum, or one or more of rare earth metals and mixtures thereof. The hydrogen-formed silica alumina has either a three-dimensional or channel pore structure crystal lattice framework. The three-dimensional aluminosilicates include both synthetic and naturally occurring silica aluminas such as faujasites, which include X-type, Y-type, ultrastable-Y, and the like. L-type, omega-type, and mordenite are examples of the channel pore structure crystalline aluminosilicates. Mordenite, in either naturally occurring or synthetic form are preferred, particularly with a silica to alumina ratio of at least 16:1. The hydrogen form aluminosilicate may be present in an amount within the range of 50 to about 99.5 wt. %, preferably within the range of 75 to about 95 wt. %, and a refractory inorganic oxide may be present in an amount within the range of from 25 to about 50 wt. %.

Operating conditions within the isomerization zone are selected to maximize the production of isoalkane product from the normal hexane and normal pentane components. Temperatures within the reaction zone will usually range from about 40–320° C. (100–600° F.). Lower reaction temperatures are generally preferred since they usually favor equilibrium mixtures of isoparaffins versus normal paraffins. Lower temperatures are particularly useful in processing feeds composed of pentanes and hexanes where the lower temperatures favor equilibrium mixtures having the highest concentration of the most branched isoalkanes. When the stream entering the isomerization zone contains primarily pentanes and hexanes, temperatures in the range of from 60 to 160° C. are preferred. Higher reaction temperatures increase catalyst activity and promote the isomerization of $C_4$ hydrocarbons. The reaction zone may be maintained over a wide range of pressures. Pressure conditions in the isomerization of $C_4$–$C_6$ paraffins range from 700 to 7000 Kpag. Preferred pressures for this process are in the range of from 2000 to 3000 Kpag. The feed rate to the reaction zone can also vary over a wide range. These conditions include liquid hourly space velocities ranging from 0.5 to 12 $hr^{-1}$, however, space velocities between 1 and 6 $hr^{-1}$ are preferred. The isomerization zone will usually operate at a LHSV of about 1.5.

Operation of the reaction zone with the preferred chlorided platinum-alumina catalyst also requires the presence of a small amount of an organic chloride promoter. The organic chloride promoter serves to maintain a high level of active chloride on the catalyst as low levels are continuously stripped off the catalyst by the hydrocarbon feed. The concentration of promoter in the reaction zone is maintained at from 30 to 300 ppm. The preferred promoter compound is trichloroethane. Other suitable promoter compounds include oxygen-free decomposable organic chlorides such as propyldichloride, butylchloride, and chloroform to name only a few of such compounds. The need to keep the reactants dry is reinforced by the presence of the organic chloride compound that converts to hydrogen chloride. As long as the process streams are kept dry, there will be no adverse effect from the presence of hydrogen chloride.

The isomerization zone usually includes a two-reactor system with a first stage reactor and a second stage reactor in the reaction zone. The catalyst used in the process is distributed equally between the two reactors. It is not necessary that the reaction is carried out in two reactors but the use of two reactors confers several benefits on the process. The use of two reactors and specialized valving allows partial replacement of the catalyst system without taking the isomerization unit off stream. For the short periods of time during which replacement of catalyst may be necessary, the entire flow of reactants may be processed through only one reaction vessel while catalyst is replaced in the other. The use of two reaction zones also aids in maintaining lower catalyst temperatures. This is accomplished by having any exothermic reaction such as hydrogenation of unsaturates performed in a first reaction vessel with the rest of the reaction carried out in a final reaction vessel at more favorable temperature conditions.

The effluent from the reactors enters a stabilizer that removes light gases and butane from the effluent (not shown). The amount of butane taken off from the stabilizer will vary depending upon the amount of butane entering the process. The stabilizer normally runs at a pressure of from 800 to 1700 Kpaa.

When the isomerization zone is operated with a high hydrogen to hydrocarbon molar ratio, a separator is usually placed ahead of the stabilizer. A hydrogen-rich recycle gas stream is recovered from the separator and recycled for combination with the feed entering the isomerization zone. When the isomerization zone operates with very low hydrogen to hydrocarbon molar ratios the separator is not needed and the effluent from the isomerization zone may enter the stabilizer directly.

The bottoms stream from the stabilizer provides an isomerization zone effluent stream comprising $C_5$ and higher boiling hydrocarbons that include normal paraffins for recycle and isoparaffin products. The chlorides, which may be present in the reaction zone, will usually pose no problem for the sorbent in the adsorption zone. In normal operation, any chlorides that are present in the effluent from the isomerization zone will be removed in the overhead from the stabilizer. However, where the isomerization zone or separators downstream from the isomerization are subject to upsets, it may be desirable to provide a guard bed of some type to treat the stabilizer bottoms and prevent any carryover of chloride compounds into the adsorption section. The isomerization zone effluent is carried in line 20 and is combined with line 14 to form the combined feed 13 to the adsorption section 30. As discussed above, in the adsorption section, the isomerized products are separated into the raffinate stream, line 22, which is conducted to a fractionation zone.

The fractionation zone serves a variety of purposes. It provides an overhead product stream that contains a high concentration of isopentane and dimethylbutanes as product isomerate. In FIG. 1, the product isomerate is withdrawn from the fractionation zone in line 34. Typically, the research octane number of the product stream will be between 89 and 93. The isomerate product stream may also contain low concentrations of normal pentane, normal hexane and monomethylpentanes. These relatively lower octane hydrocarbons are reduced by the operation of the adsorption section, which preferentially adsorbs normal pentane and recycles the normal pentanes to the isomerization zone in the extract stream. Similarly, the withdrawal of normal hexane and monomethylpentanes in large amounts from the fractionation zone for use as a desorbent material in the adsorption section, which also eventually is recycled to the isomerization zone, serves to lower the amount of low-octane components in the product isomerate.

Heavier hydrocarbons are withdrawn from the fractionation column as a heavy hydrocarbon stream. Because the majority of the heavy hydrocarbons were removed in naphtha splitter column 12 column, the heavy hydrocarbon stream from the fractionation column is of relatively reduced volume, more on the order of a drag stream. For the single column deisohexanizer, this heavy hydrocarbon stream is withdrawn as a drag stream from the bottom in line 36. Where a full boiling range naphtha is used as the feed to the overall process, the heavy hydrocarbon stream will comprise a $C_7+$ naphtha. This bottoms stream will sometimes be used as part of the feed in a reforming zone.

A stream containing desorbent to be used in the adsorption section is preferably removed as a sidecut from a single fractionation column. The stream contains primarily normal hexane and monomethylpentanes. In FIG. 1, line 32 is shown as a sidecut stream from the deisohexanizer column 26. Line 32 provides a desorbent for the adsorption section that is passed from line 32 to the adsorption section through combination with line 16. Depending on the conditions in the adsorption section and the isomerization zone, the amount of the desorbent available through line 32 may exceed that needed in the adsorption section. This excess desorbent may be diverted from line 32 to the previously described line 24 to enter the isomerization zone directly as part of the feed to the isomerization zone feed (not shown). The withdrawal of the desorbent as a liquid sidecut from the deisohexanizer has the advantage of disengaging desorbent from the raffinate stream at low utility cost.

Excess desorbent in line 32 is present in the deisohexanizer as part of the normal hexane that has been charged to the fractionation zone. However, it may be possible to eliminate the excess desorbent from the fractionation zone by changing the operation of the splitter column when one is provided.

In this invention, the extract stream from the adsorption section does not enter any separation section for the recovery of the displacement fluid or desorbent. At least a portion of the extract stream is flowed directly to the isomerization zone. The direct routing of the extract stream eliminates the need for a separation column and the equipment associated therewith, which significantly reduces the cost of the adsorption section. Prior processes have provided a column for the separation of desorbent from the extract stream in the belief that the process could not be economically operated without such a separation.

In a specific embodiment of the invention, the deisohexanizer may be a divided wall fractional distillation column. Within the divided wall fractional distillation column are two parallel fractionation zones. A first fractionation zone occupies a large portion of the left-hand side of the midsection of the fractional distillation column. Note that the terms "left-hand" and "right-hand" are used herein as relative to the drawings. In actual practice, the placement of the zones as to the left side or the right side of the column is not critical. This first fractionation zone is separated from a parallel second fractionation zone occupying the other half of the column cross section by a substantially fluid tight vertical wall. The vertical wall is not necessarily centered in the column and the two fractionation zones may differ in cross sectional area or shape. The vertical wall divides a large vertical portion of the column into two parallel fractionation zones. The two zones are isolated from each other for the height of this wall, but communicate at both the top and bottom ends of the column. There is no direct vapor or liquid flow between the two fractionation zones through the dividing wall, but the upper end of the fractionation zone receiving the raffinate product is open to the internal volume of the distillation column containing an undivided fractionation zone preferably having additional trays. Liquid may pass under the dividing wall at the bottom of the two fractionation sections although vapor flow is preferably restricted. Thus, vapor and liquid can freely move around the wall between the two portions of the column. During operation, the raffinate is separated in the first fractionation zone with the more volatile compounds moving upward out of the left-hand first fractionation zone and emerging into the undivided upper portion of the distillation column. As with the first fractionation zone, the upper end of the right-hand second zone is in open communication with the upper section of the distillation column, which preferably contains additional fractionation trays extending across the entire column cross section.

The raffinate stream contains isopentane, 2,2-dimethylbutane, 2,3-dimethylbutane, 2-methylpentane, 3-methylpentane, methylcyclopentane, cyclohexane and $C_7+$. For ease of discussion, the raffinate product stream components will be grouped according to boiling point, which is the main factor in determining their behavior in the fractional distillation column. The components having relatively low boiling points will be labeled Group A and will consist of 2,3-dimethylbutane, 2,2-dimethylbutane, and isopentane. Group A contains high-octane components that are desired products of the overall isomerization process. The mid-range boiling components will be labeled Group B and contains 2-methylpentane, 3-methylpentane, and normal hexane. Group B contains lower octane components that are used as desorbent and would best be recycled to the isomerization zone and not included in a final isomerate product. Separating and recycling the 2-methylpentane, 3-methylpentane and normal hexane results in the final product having a higher overall octane value. The components having relatively high boiling points will be labeled Group C and will consist of methylcyclopentane, cyclohexane, and $C_7+$. It is expected that Group C may be small relative to groups A and B, and may constitute a drag stream.

The raffinate stream from the adsorption section is introduced into a first vertical fractionation zone occupying a large portion of the left-hand side of the midsection of the dividing wall deisohexanizer. The Group A components along with a portion of the Group B components present in the raffinate stream are driven upward in the first fractionation zone and enter the top of the column. The top of the column is a purification zone which is designed to separate the Group A components from the Group B components. A Group A-rich stream is removed from the top of the dividing wall and passed through an overhead condenser (not shown) to form liquid delivered to the receiver (not shown). A liquid phase stream of Group A components is removed from the receiver and divided into a first portion which is returned to the top of the dividing wall fractionation column as reflux and a second portion which is removed from the process in line 34. As used herein the term "rich" is intended to indicate a concentration of the indicated compound or class of compounds greater than 50 and preferably greater than 75 mol percent.

The bottom of the dividing wall column also comprises an undivided fractionation zone. This zone can receive liquid draining from both the first and second fractionation zones. This liquid is subjected to fractional distillation which drives the Group B components upwards as vapor while concentrating the less volatile Group C components into a bottoms liquid that is removed from the dividing wall fractionation column in line 36. This separation is effected through the use of a reboiler (not shown) providing vapor to the bottom undivided fractionation zone. The Group B components are withdrawn from the dividing wall fractionation column in a side draw from the right-hand side fractionation zone. The Group B components are recycled to the adsorption section for use as a desorbent and then to the isomerization zone, for conversion into components having a higher octane value.

In yet a more specific embodiment of the invention, the undivided bottom section of the dividing wall fractionation column may be separated from the two parallel fractionation zones by a gas flow control or gas trap out tray located just below the bottom of the wall. A slight gap at this point allows horizontal liquid flow between the parallel fractionation zones. This tray may have liquid sealed perforations allowing the normal downward flow of liquid, but its structure is such that the upward flow of vapor is at least greatly restricted. The tray may totally block the upward vapor flow. The use of this tray is preferred as it provides a means to positively control the division of the upward gas flow between the two fractionation zones, which is a prime means of controlling performance of the two zones. The total vapor flow is, therefore, preferably removed from the column via a line and divided between two separate lines that feed the vapor to the bottom of the two parallel fractionation zones. The gas flow may be controlled by one or more flow control valves or by adjusting the relative liquid levels in the bottom of the two zones. This is described in some detail in U.S. Pat. No. 4,230,533 B1 for a slightly different arrangement.

Note that the naphtha splitter discussed in detail above may also be in the form of a dividing wall fractionation column as discussed in relation to the deisohexanizer column. A dividing wall naphtha splitter would be structured and would operate as described above for the dividing wall deisohexanizer. However, the separation achieved may be somewhat different. For example, a first group separated into the overhead stream would contain most of the pentanes, a second group separated into a sidecut stream would contain most of the hexanes, and a third group separated into the bottoms stream would contain most of the heptanes and higher boiling material.

EXAMPLE

The ability of this isomerization zone and adsorption section combination to operate without extract or raffinate columns and provide a high-octane isomerate product is demonstrated by the following example. This example consists of engineering calculations that are based on experience from the operation of similar components in commercial processing units. This example is arranged in accordance with the isomerization zone and adsorption section shown in FIG. 2 and will be described using the reference numbers appearing therein. Table 1 shows the flowing composition in Kgmole/hr of different streams shown in FIG. 2. A $C_5+$ naphtha feed having the composition given in Table 1 for stream 10 is fed into a naphtha splitter column 12 at a temperature of 85° C. and a pressure of 500 Kpaa. Naphtha splitter column 12 is arranged with 40 trays and operates with a molar reflux to feed ratio of 1.50. A bottoms stream is taken from splitter 12 by line 18 at a temperature of 156° C. and a pressure of 280 Kpaa which contains components having a higher boiling point than normal hexane. An overhead stream is taken by line 15 at a pressure of 200 Kpaa and a temperature of 49° C. An side-cut stream is taken by line 16 at a pressure of 240 Kpaa and a temperature of 97° C.

TABLE 1

| Components Kgmole/hr | STREAM (FIG. 2) | | | | | | | | | |
|---|---|---|---|---|---|---|---|---|---|---|
| | 10 | 15 | 16 | 25 | 20 | 24 | 22 | 32 | 36 | 34 |
| Isobutane | 8.1 | 8.1 | 0.0 | 8.5 | 11.3 | 0.4 | 10.9 | 0.0 | 0.0 | 10.9 |
| n-Butane | 33.0 | 33.0 | 0.0 | 78.9 | 46.5 | 45.9 | 0.7 | 0.0 | 0.0 | 0.7 |
| Isopentane | 92.7 | 90.5 | 2.2 | 100.3 | 247.8 | 9.8 | 240.2 | 0.0 | 0.0 | 240.2 |
| n-Pentane | 152.2 | 143.0 | 9.1 | 219.0 | 78.3 | 76.0 | 11.5 | 0.0 | 0.0 | 11.5 |
| Cyclopentane | 9.6 | 8.2 | 1.4 | 9.5 | 6.6 | 1.3 | 6.8 | 0.1 | 0.0 | 6.7 |
| 2,2-Dimethylbutane | 1.9 | 1.4 | 0.5 | 17.3 | 188.0 | 15.9 | 184.7 | 11.8 | 0.0 | 172.9 |
| 2,3-Dimethylbutane | 9.7 | 4.2 | 5.3 | 42.6 | 62.7 | 38.4 | 71.9 | 42.3 | 0.0 | 29.6 |
| 2-Methylpentane | 63.2 | 19.0 | 41.9 | 216.7 | 201.3 | 197.7 | 253.7 | 207.9 | 0.0 | 45.8 |
| 3-Methylpentane | 55.2 | 7.3 | 44.6 | 156.0 | 106.5 | 148.7 | 147.9 | 145.2 | 0.0 | 2.7 |
| n-Hexane | 142.3 | 2.8 | 121.0 | 191.3 | 68.2 | 188.5 | 244.6 | 244.0 | 0.6 | 0.0 |
| Methylcyclopentane | 25.0 | 0.2 | 19.4 | 41.5 | 21.6 | 41.3 | 33.5 | 33.1 | 0.4 | 0.0 |
| Cyclohexane | 20.4 | 0.1 | 8.6 | 24.6 | 21.8 | 24.5 | 28.5 | 22.4 | 6.1 | 0.0 |
| Benzene | 8.3 | 0.1 | 6.2 | 6.2 | 0.0 | 6.1 | 1.9 | 1.9 | 0.0 | 0.0 |
| Isoheptane | 94.9 | 0.0 | 5.5 | 5.7 | 2.2 | 5.7 | 2.6 | 0.1 | 2.5 | 0.0 |
| n-Heptane | 106.3 | 0.0 | 1.0 | 0.8 | 0.0 | 0.8 | 0.2 | 0.0 | 0.2 | 0.0 |
| Other $C_7+$ | 613.9 | 0.0 | 1.5 | 1.5 | 9.0 | 1.5 | 8.8 | 0.0 | 8.8 | 0.0 |
| Total | 1436.7 | 317.9 | 268.2 | 1120.4 | 1071.8 | 802.5 | 1248.4 | 708.8 | 18.6 | 521.0 |

The overhead components carried by line 15 are combined with an absorption zone effluent carried by line 24. The flowing composition of line 25 is the flowing composition of a combined feed that enters an isomerization zone at a temperature of 146° C. and a pressure of 3204 Kpaa. In the isomerization zone, the combined feed is contacted with an isomerization catalyst that comprises a chlorided platinum-alumina catalyst at a liquid hourly space velocity of 1.0. As the combined feed enters the isomerization zone, it is combined with hydrogen in an amount to produce a hydrogen/hydrocarbon ratio of 0.05 at the outlet of the isomerization section. The isomerization section includes a two-reactor system that operates at a pressure of 3204 Kpaa. A stabilized effluent in line 20 is recovered from the isomerization zone 28 and fed to an adsorption section 30.

The adsorption section is arranged with an eight-bed adsorption column filled with a zeolite adsorbent of the Ca-A type. The adsorption section operates at a cycle time of less than 30 minutes for a complete sequence of all the zones through the beds of adsorbent. An operating temperature of 120° C. and an operating pressure of 1442 Kpaa are maintained within the adsorption section. The extract stream taken by line 24 is withdrawn from the adsorption section along with a raffinate stream in line 22. The raffinate stream is transferred without intermediate separation into the dividing wall deisohexanizer column 26.

Dividing wall deisohexanizer column 26 is arranged with 100 trays and operates with a molar reflux to net deisohexanizer feed ratio of 2.0. The raffinate stream 22 enters the deisohexanizer on one side of the dividing wall and a desorbent stream in line 32 is withdrawn from the other side of the dividing wall in the deisohexanizer as a sidecut. The desorbent taken by line 32 is combined with line 16 for use as a desorbent in the adsorption section. A bottoms stream in line 36 is withdrawn from the dividing wall deisohexanizer column and may be used as the feed to a reforming process. The contents of line 36 are taken from the column at a temperature of 131° C. and a pressure of 230 Kpaa. The remaining column output is taken overhead by line 34 as an isomerate product stream. The contents of line 34 are recovered at a temperature of 48° C. and a pressure of 150 Kpaa. The isomerate product has the properties given in Table 2.

TABLE 2

| | |
|---|---|
| RONC | 92.0 |
| MONC | 90.7 |
| RVP | 104 kPa |
| S.G. | 0.627 |

This example shows that the isomerate product has a high octane number, about 3 to 5 octane numbers higher than that usually achievable with conventional recycle isomerization schemes. Therefore, the flow arrangement of this invention will improve the operation of an isomerization zone and adsorption section combination by increasing the octane of the isomerate obtained therefrom and simplifying the overall operation of the combination process.

What is claimed is:

1. A process for the isomerization of a feed stream comprising at least $C_5$–$C_6$ hydrocarbons said process comprising:

a) separating, in a first fractionation zone, said feed stream comprising at least $C_5$–$C_6$ hydrocarbons into a first stream comprising normal and branched pentanes and lighter boiling hydrocarbons and a second stream comprising normal and branched hexanes;

b) contacting at least a portion of the first stream and at least a portion of an isomerization zone effluent with an adsorbent in an adsorption section, selectively adsorbing normal paraffins, and producing a raffinate stream having a decreased concentration of at least one normal paraffin component relative to said portion of the first stream combined with said portion of the isomerization zone effluent, and the adsorbent having normal paraffins adsorbed thereon;

c) desorbing the normal paraffins from the adsorbent using the second stream and at least a portion of a second desorbent stream containing normal hexane and monomethylpentane from a second fractionation zone to generate an extract stream containing at least normal pentane, normal hexane, and monomethylpentanes;

d) isomerizing at least a portion of the extract stream in an isomerization zone containing an isomerization catalyst at isomerization conditions to form said-isomerization zone effluent comprising at least $C_5$ and $C_6$ isomerized products; and e) separating, in a second fractionation zone, said raffinate stream into an isomerate stream, a heavy hydrocarbon stream, and said stream containing normal hexane and monomethylpentane.

2. The process of claim 1 further comprising said feed stream containing $C_7$ and higher boiling hydrocarbons and separating, in the first fractionation zone, a third stream comprising components from said feed stream having boiling points higher than that of normal hexane.

3. The process of claim 1 wherein said adsorption section comprises a simulated moving bed adsorption zone.

4. The process of claim 1 further comprising passing said isomerization effluent directly to a stabilizer, removing $C_4$ and lighter hydrocarbons from said effluent and passing the remainder of the effluent to said adsorption section.

5. The process of claim 1 wherein the adsorbent in said adsorbent section comprises a Ca-A zeolite.

6. The process of claim 1 wherein said adsorption section operates in the liquid phase.

7. The process of claim 1 wherein said isomerization catalyst comprises alumina having from 0.01 to 0.25 wt. % platinum and from 2 to 10 wt. % of a chloride component.

8. The process of claim 3 wherein said adsorption section comprises at least one bed of adsorbent, the total quantity of adsorbent is divided into at least three operationally distinct zones of adsorbent, said first stream and said effluent are charged to a different zone from that of said second stream, and the position of the zones relative to said total quantity of said adsorbent is at least intermittently varied by changing withdrawal and input points for said first stream and said second stream.

9. The process of claim 1 wherein said raffinate stream has a decreased concentration of normal pentane relative to said first stream.

10. The process of claim 1 wherein said second fractionation zone comprises a single deisohexanizer column.

11. The process of claim 1 wherein the second fractionation zone comprises a dividing wall deisohexanizer column.

12. The process of claim 1 wherein the first fractionation zone comprises a naphtha splitter column.

13. The process of claim 1 wherein the first fractionation zone comprises a dividing wall naphtha splitter column.

14. A process for the isomerization of a feed stream comprising at least $C_5$–$C_7$ hydrocarbons said process comprising:
  a) separating, in a naphtha splitter column, said feed stream comprising at least $C_5$–$C_7$ hydrocarbons into an adsorption section feed stream comprising normal and branched pentanes and lighter boiling hydrocarbons, a first desorbent stream comprising normal and branched hexanes, and a bottoms stream comprising components from said feed stream having boiling points higher than normal hexane;
  b) contacting at least a portion of the adsorption section feed stream and at least a portion of an isomerization zone effluent with an adsorbent in a simulated moving bed adsorption section, selectively adsorbing normal paraffins, and producing a raffinate stream having a decreased concentration of at least one normal paraffin component relative to said portion of the adsorption section feed stream combined with said portion of the isomerization zone effluent, and the adsorbent having normal paraffins adsorbed thereon;
  c) desorbing the normal paraffins from the adsorbent using the first desorbent stream and at least a portion of a second desorbent stream containing normal hexane and monomethylpentane from a deisohexanizer column to generate an extract stream containing at least normal pentane, normal hexane, and monomethylpentanes;
  d) isomerizing at least a portion of the extract stream in an isomerization zone containing an isomerization catalyst at isomerization conditions and separating and removing $C_4$ and lighter boiling hydrocarbons to form said isomerization zone effluent comprising at least $C_5$ and $C_6$ isomerized products; and
  e) separating, in the deisohexanizer column, said raffinate stream into an overhead isomerate stream, a bottoms heavy hydrocarbon stream, and, as a sidecut from the deisohexanizer column, said second desorbent stream.

15. The process of claim 14 further comprising operating the simulated moving bed adsorption section by:
  a) maintaining a net fluid flow through at least three operationally distinct and serially interconnected zones of adsorbent in said adsorption section;
  b) maintaining an adsorption zone in said adsorption section, said adsorption zone being defined by the adsorbent located between a feed input stream at an upstream boundary of said zone, and a raffinate output stream at a downstream boundary of said zone;
  c) maintaining a purification zone immediately upstream from said adsorption zone, said purification zone being defined by the adsorbent located between an extract output stream at an upstream boundary of said purification zone and said feed input stream at a downstream boundary of said purification zone;
  d) maintaining a desorption zone immediately upstream from said purification zone, said desorption zone being defined by the adsorbent located between a desorbent input stream at an upstream boundary of said zone and said extract output stream at a downstream boundary of said zone;
  e) passing said portion of the adsorption section feed stream and said portion of an isomerization zone effluent feed into said adsorption zone at adsorption conditions to effect the selective adsorption of said normal pentane by said adsorbent in said adsorption zone and withdrawing a raffinate output stream from said adsorption zone;
  f) passing at least a portion of said first and second desorbent streams into said desorption zone at desorption conditions to effect the displacement of said normal pentane from the adsorbent in said desorption zone;
  g) withdrawing an extract output stream comprising said normal paraffins and desorbant from said desorption zone;
  h) withdrawing a raffinate output stream comprising isoparaffins and desorbent from said adsorption zone; and
  i) periodically advancing through said column of adsorbent in a downstream direction with respect to fluid flow in said adsorption zone, the feed input stream, raffinate output stream, desorbent input stream and extract output stream to effect the shifting of zones through said adsorbent and the production of extract output and raffinate output streams.

16. The process of claim 14 wherein the naphtha splitter column is a dividing wall naphtha splitter column.

17. The process of claim 14 wherein the deisohexanizer column is a dividing wall deisohexanizer column.

18. A process for the isomerization of a feed stream comprising at least $C_5$–$C_6$ hydrocarbons said process comprising:

a) separating, in a first fractionation zone, said feed stream comprising at least $C_5$–$C_6$ hydrocarbons into a first stream comprising normal and branched pentanes and lighter boiling hydrocarbons and a second stream comprising normal and branched hexanes;

b) contacting at least a portion of an isomerization zone effluent with an adsorbent in an adsorption section, selectively adsorbing normal paraffins, and producing a raffinate stream having a decreased concentration of at least one normal paraffin component relative to said portion of the isomerization zone effluent, and the adsorbent having normal paraffins adsorbed thereon;

c) desorbing the normal paraffins from the adsorbent using the second stream and at least a portion of a second desorbent stream containing normal hexane and monomethylpentane from a second fractionation zone to generate an extract stream containing at least normal pentane, normal hexane, and monomethylpentanes;

d) isomerizing at least a portion of the extract stream and at least a portion of the first stream in an isomerization zone containing an isomerization catalyst at isomerization conditions to form said isomerization zone effluent comprising at least $C_5$ and $C_6$ isomerized products; and e) separating, in a second fractionation zone, said raffinate stream into an isomerate stream, a heavy hydrocarbon stream, and said stream containing normal hexane and monomethylpentane.

19. The process of claim 18 further comprising said feed stream containing $C_7$ and higher boiling point hydrocarbons and separating, in the first fractionation zone, a third stream comprising components from said feed stream having boiling points above normal hexane.

20. The process of claim 18 wherein said adsorption section comprises a simulated moving bed adsorption zone.

21. The process of claim 18 further comprising passing said isomerization effluent directly to a stabilizer, removing $C_4$ and lighter hydrocarbons from said effluent and passing the remainder of the effluent to said adsorption section.

22. The process of claim 18 wherein the adsorbent in said adsorbent section comprises a Ca-A zeolite.

23. The process of claim 18 wherein said adsorption section operates in the liquid phase.

24. The process of claim 18 wherein said isomerization catalyst comprises alumina having from 0.01 to 0.25 wt. % platinum and from 2 to 10 wt. % of a chloride component.

25. The process of claim 20 wherein said adsorption section comprises at least one bed of adsorbent, the total quantity of adsorbent is divided into at least three operationally distinct zones of adsorbent, said effluent is charged to a different zone from that of said second stream, and the position of the zones relative to said total quantity of said adsorbent is at least intermittently varied by changing withdrawal and input points for said first stream and said second stream.

26. The process of claim 18 wherein said raffinate stream has a decreased concentration of normal pentane relative to said first stream.

27. The process of claim 18 wherein said second fractionation zone comprises a single deisohexanizer column.

28. The process of claim 18 wherein the second fractionation zone comprises a dividing wall deisohexanizer column.

29. The process of claim 18 wherein the first fractionation zone comprises a naphtha splitter column.

30. The process of claim 18 wherein the first fractionation zone comprises a dividing wall naphtha splitter column.

31. A process for the isomerization of a feed stream comprising at least $C_5$–$C_7$ hydrocarbons said process comprising:

a) separating, in a naphtha splitter column, said feed stream comprising at least $C_5$–$C_7$ hydrocarbons into an isomerization zone feed stream comprising normal and branched pentanes and lighter boiling hydrocarbons, a first desorbent stream comprising normal and branched hexanes, and a bottoms stream containing components having higher boiling points than normal hexane;

b) contacting at least a portion of an isomerization zone effluent with an adsorbent in a simulated moving bed adsorption section, selectively adsorbing normal paraffins, and producing a raffinate stream having a decreased concentration of at least one normal paraffin component relative said portion of the isomerization zone effluent, and the adsorbent having normal paraffins adsorbed thereon;

c) desorbing the normal paraffins from the adsorbent using the first desorbent stream and at least a portion of a second desorbent stream containing normal hexane and monomethylpentane from a deisohexanizer column to generate an extract stream containing at least normal pentane, normal hexane, and monomethylpentanes;

d) isomerizing at least a portion of the extract stream and at least a portion of the isomerization zone feed stream from the naphtha splitter column in an isomerization zone containing an isomerization catalyst at isomerization conditions and separating and removing $C_4$ and lower boiling hydrocarbons to form said isomerization zone effluent comprising at least $C_5$ and $C_6$ isomerized products; and e) separating, in a deisohexanizer column, said raffinate stream into an overhead isomerate stream, a bottoms heavy hydrocarbon stream, and the side cut second desorbent stream containing normal hexane and monomethylpentane.

32. The process of claim 31 further comprising operating the simulated moving bed adsorption section by:

a) maintaining a net fluid flow through at least three operationally distinct and serially interconnected zones of adsorbent in said adsorption section;

b) maintaining an adsorption zone in said adsorption section, said adsorption zone being defined by the adsorbent located between a feed input stream at an upstream boundary of said zone, and a raffinate output stream at a downstream boundary of said zone;

c) maintaining a purification zone immediately upstream from said adsorption zone, said purification zone being defined by the adsorbent located between an extract output stream at an upstream boundary of said purification zone and said feed input stream at a downstream boundary of said purification zone;

d) maintaining a desorption zone immediately upstream from said purification zone, said desorption zone being defined by the adsorbent located between a desorbent input stream at an upstream boundary of said zone and said extract output stream at a downstream boundary of said zone;

e) passing said portion of the isomerization zone effluent into said adsorption zone at adsorption conditions to effect the selective adsorption of said normal pentane by said adsorbent in said adsorption zone and withdrawing a raffinate output stream from said adsorption zone;

f) passing at least a portion of said first and second desorbent streams into said desorption zone at desorption conditions to effect the displacement of said normal pentane from the adsorbent in said desorption zone;

g) withdrawing an extract output stream comprising said normal paraffins and desorbent from said desorption zone;

h) withdrawing a raffinate output stream comprising isoparaffins and desorbent from said adsorption zone; and i) periodically advancing through said column of adsorbent in a downstream direction with respect to fluid flow in said adsorption zone, the feed input stream, raffinate output stream, desorbent input stream and extract output stream to effect the shifting of zones through said adsorbent and the production of extract output and raffinate output streams.

33. The process of claim 31 wherein the naphtha splitter column is a dividing wall naphtha splitter column.

34. The process of claim 31 wherein the deisohexanizer column is a dividing wall deisohexanizer column.

* * * * *